United States Patent
Zhang

(10) Patent No.: US 12,224,054 B2
(45) Date of Patent: Feb. 11, 2025

(54) DIET RECOMMENDATION METHOD, DEVICE, STORAGE MEDIUM AND ELECTRONIC DEVICE

(71) Applicant: BOE TECHNOLOGY GROUP CO., LTD., Beijing (CN)

(72) Inventor: Xiying Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 279 days.

(21) Appl. No.: 17/614,454

(22) PCT Filed: Dec. 25, 2020

(86) PCT No.: PCT/CN2020/139313
§ 371 (c)(1),
(2) Date: Nov. 26, 2021

(87) PCT Pub. No.: WO2022/133985
PCT Pub. Date: Jun. 30, 2022

(65) Prior Publication Data
US 2022/0399098 A1     Dec. 15, 2022

(51) Int. Cl.
G16H 20/60  (2018.01)
G09B 19/00  (2006.01)
G16H 50/20  (2018.01)

(52) U.S. Cl.
CPC ......... *G16H 20/60* (2018.01); *G09B 19/0092* (2013.01); *G16H 50/20* (2018.01)

(58) Field of Classification Search
CPC .................. G16H 20/60; G16H 50/20; G16H 10/00–80/00; G09B 19/0092
See application file for complete search history.

(56) References Cited

U.S. PATENT DOCUMENTS

| | | | |
|---|---|---|---|
| 11,144,957 B1* | 10/2021 | Raak | G06Q 30/0631 |
| 2013/0216982 A1* | 8/2013 | Bennett | A61B 5/4866 |
| | | | 434/127 |
| 2015/0279235 A1* | 10/2015 | Yamada | G06Q 50/10 |
| | | | 434/127 |
| 2019/0073601 A1* | 3/2019 | Alkan | G06N 20/00 |

(Continued)

FOREIGN PATENT DOCUMENTS

| | | | |
|---|---|---|---|
| CN | 104731846 A | * | 6/2015 |
| CN | 105787500 A | | 7/2016 |

(Continued)

OTHER PUBLICATIONS

Karpov et al., "Automated Methodology for Optimizing Menus in Personalized Nutrition," (IJACSA) International Journal of Advanced Computer Science and Applications, vol. 10, No. 11, 2019. (Year: 2019).*

(Continued)

*Primary Examiner* — Jonathon A. Szumny
(74) *Attorney, Agent, or Firm* — Perilla Knox & Hildebrandt LLP; Kenneth A. Knox

(57) ABSTRACT

A diet recommendation method, device, storage medium and electronic device are described. The diet recommendation method includes: obtaining historical dining data; and determining a target recommended recipe by using a recommendation model based on multiple candidate foods and the historical dining data.

14 Claims, 6 Drawing Sheets

(56) References Cited

U.S. PATENT DOCUMENTS

| | | | | |
|---|---|---|---|---|
| 2019/0221303 A1* | 7/2019 | Bennett | .................. | G16H 10/20 |
| 2019/0295440 A1* | 9/2019 | Hadad | .................. | G06F 40/295 |
| 2020/0098466 A1* | 3/2020 | Murdoch | ............... | G16H 20/60 |
| 2021/0209963 A1* | 7/2021 | Hill | ........................ | G16H 50/30 |
| 2021/0375427 A1* | 12/2021 | Neumann | ............... | G16H 20/60 |
| 2022/0319667 A1* | 10/2022 | Wang | .................... | G16H 30/40 |

FOREIGN PATENT DOCUMENTS

| | | | | | |
|---|---|---|---|---|---|
| CN | 105843799 A | | 8/2016 | | |
| CN | 107423421 A | | 12/2017 | | |
| CN | 108597582 A | * | 9/2018 | ........... | G06F 18/214 |
| CN | 109243580 A | | 1/2019 | | |
| CN | 109346153 A | | 2/2019 | | |
| CN | 109493944 A | * | 3/2019 | | |
| CN | 109545327 A | * | 3/2019 | | |
| CN | 110287306 A | | 9/2019 | | |
| CN | 110310721 A | | 10/2019 | | |
| CN | 110504019 A | * | 11/2019 | | |
| CN | 110781413 A | | 2/2020 | | |
| CN | 111159539 A | | 5/2020 | | |
| CN | 111241292 A | | 6/2020 | | |
| CN | 111402996 A | | 7/2020 | | |
| CN | 111524576 A | * | 8/2020 | ............... | G09B 7/04 |
| CN | 111652044 A | * | 9/2020 | | |
| CN | 112002377 A | * | 11/2020 | ............. | G06N 20/20 |
| JP | 2015153181 A | | 8/2015 | | |
| KR | 20210008268 A | * | 1/2021 | | |
| WO | WO-2014160298 A1 | * | 10/2014 | ............. | G06F 17/30 |
| WO | 2020076874 A1 | | 4/2020 | | |
| WO | 2020111787 A1 | | 6/2020 | | |

OTHER PUBLICATIONS

Orlov et al., "Digital Nutrition: Spectral Portraits of Optimal Diet," Scientific Visualization, 2020, vol. 12, No. 2, pp. 139-150, DOI: 10.26583/sv.12.2.11. (Year: 2020).*

Written Opinion for PCT Patent Application No. PCT/CN2020/139313 mailed Sep. 27, 2021.

* cited by examiner

DIET RECOMMENDATION METHOD, DEVICE, STORAGE MEDIUM AND ELECTRONIC DEVICE

CROSS-REFERENCE TO RELATED APPLICATION

This application is a national phase application under 35 U.S.C. § 371 of International Application No. PCT/CN2020/139313, filed Dec. 25, 2020, the contents of which being incorporated herein by reference in their entirety for all purposes.

TECHNICAL FIELD

The present disclosure relates to the technical field of data processing and, in particular, to a diet recommendation method, a diet recommendation device, a non-transitory computer-readable storage medium, and an electronic device.

BACKGROUND

With the improvement of living standards, people pay more and more attention to their own health. And a person's health is closely related to eating habits. Whether the diet is healthy and reasonable has become a topic of great concern to people in daily life.

Therefore, it is very necessary to provide a highly accurate diet recommendation method for users to recommend recipes scientifically and reasonably.

It should be noted that the information disclosed in the Background section above is only for enhancing the understanding of the background of the present disclosure, and thus may include information that does not constitute prior art known to those of ordinary skill in the art.

SUMMARY

The present disclosure provides a diet recommendation method, a diet recommendation device, a computer-readable storage medium, and an electronic device.

The present disclosure provides a diet recommendation method, which may be applied to a server (e.g., a server computing device) or a terminal device (e.g., a terminal computing device), including:
  obtaining historical dining data of a user; and
  determining, based on multiple candidate foods and the historical dining data, a target recommended recipe by using a recommendation model.

In an exemplary embodiment of the present disclosure, the determining, based on the multiple candidate foods and the historical dining data, the target recommended recipe by using the recommendation model includes:
  constructing a hierarchical graph model based on the multiple candidate foods; and
  determining, based on the historical dining data, the target recommended recipe by using the hierarchical graph model according to a random walk algorithm.

In an exemplary embodiment of the present disclosure, the constructing the hierarchical graph model based on the multiple candidate foods includes:
  constructing the hierarchical graph model by taking the multiple candidate foods as nodes, and paths between the nodes as edges.

In an exemplary embodiment of the present disclosure, the determining, based on the historical dining data, the target recommended recipe by using the hierarchical graph model according to the random walk algorithm includes:
  initializing a weight of each edge in the hierarchical graph model;
  updating the weight of each edge according to the historical dining data of a user; and
  determining candidate foods contained in a path with a largest weight as the target recommended recipe.

In an exemplary embodiment of the present disclosure, the determining the candidate foods contained in the path with the largest weight as the target recommended recipe further includes:
  obtaining, based on the weight of the path corresponding to the target recommended recipe, a probability of the user selecting the target recommended recipe as a first probability value;
  obtaining probabilities of multiple other users selecting the target recommended recipe as second probability values; and
  determining a probability of the user selecting the target recommended recipe based on the first probability value and the second probability values.

In an exemplary embodiment of the present disclosure, the determining the target recommended recipe by using the recommendation model based on the multiple candidate foods and the historical dining data further includes:
  determining the target recommended recipe by using an attention mechanism model based on the multiple candidate foods and the historical dining data.

In an exemplary embodiment of the present disclosure, the determining the target recommended recipe by using the attention mechanism model based on the multiple candidate foods and the historical dining data includes:
  presetting multiple templates for a meal preparation rule of each meal based on the multiple candidate foods;
  obtaining multiple template vectors by vectorizing the multiple templates;
  determining a food of each meal in the historical dining data of a user,
  obtaining an implicit vector of each meal by vectorizing the food and performing feature extraction on the food vector;
  obtaining an enhanced target template vector by performing an operation on the implicit vector of each meal with a target template vector; and
  outputting the target recommended recipe corresponding to a target template in response to classifying the enhanced target template vector through a neural network classifier.

In an exemplary embodiment of the present disclosure, the implicit vector of each meal comprises a second vector and a third vector; the determining the food of each meal in the historical dining data of the user, and the obtaining the implicit vector of each meal by vectorizing the food and performing the feature extraction on the food vector includes:
  determining the food of each meal in the historical dining data of the user,
  obtaining a first vector of each meal by vectorizing the food;
  obtaining the second vector of each meal by performing an operation on the first vector of each meal using a first parameter matrix; and
  obtaining the third vector of each meal by performing an operation on the first vector of each meal using a second parameter matrix.

In an exemplary embodiment of the present disclosure, the method further includes:
  obtaining multiple sets of sample information, where each set of sample information comprises: the implicit vector of each meal and the multiple template vectors;
  training the attention mechanism model by taking the implicit vector of each meal as input, where probability values of the multiple template vectors are outputs, and determining a template vector with the largest probability value as the target template vector.

In an exemplary embodiment of the present disclosure, the obtaining the enhanced target template vector by performing the operation on the implicit vector of each meal with the target template vector includes:
  calculating an attention score between the target template vector and the second vector of each meal; and
  obtaining the enhanced target template vector by performing weighted average on the third vector of each meal according to the attention score corresponding to the implicit vector of each meal.

In an exemplary embodiment of the present disclosure, the method further includes:
  presetting a meal preparation rule of each meal.

In an exemplary embodiment of the present disclosure, the method further includes:
  determining a mass of each food in the target recommended recipe according to a mass of each nutrient required for each meal.

In an exemplary embodiment of the present disclosure, the determining the mass of each food in the target recommended recipe according to the mass of each nutrient required for each meal includes:
  determining the mass of each nutrient required by the user for each meal according to basic information of the user; and
  determining the mass of each food in the target recommended recipe according to the mass of each nutrient required for each meal.

In an exemplary embodiment of the present disclosure, the determining the mass of each nutrient required by the user for each meal according to the basic information of the user includes:
  determining energy required by the user for each meal according to the basic information of the user; and
  determining the mass of each nutrient required by the user for each meal according to following relationships each between the energy required by the user for each meal and a nutrient required by the user for each meal:

$$\begin{cases} nutrientCount_1 = energy * ratio_1 / param_1 \\ nutrientCount_2 = energy * ratio_2 / param_2 \\ ... \\ nutrientCount_n = energy * ratio_n / param_n \end{cases};$$

where $nutrientCount_n$ represents a mass of a $n^{th}$ nutrient, energy represents an energy value required by the user for each meal in a candidate recipe, $ratio_n$ represents a ratio coefficient of the $n^{th}$ nutrient to the energy value of each meal, and $param_n$ represents a converted energy coefficient of the $n^{th}$ nutrient; and n is a positive integer.

In an exemplary embodiment of the present disclosure, the determining the mass of each food in the target recommended recipe according to the mass of each nutrient required for each meal includes:
  determining the mass of each food in the target recommended recipe according to following relationships each between a content of a nutrient in a candidate food contained in the target recommended recipe and a mass of the nutrient required for each meal:

$$\begin{cases} fat_1 * x_1 + fat_2 * x_2 + ... + fat_m * x_m = Count_1 \\ protein_1 * x_1 + protein_2 * x_2 + ... + protein_m * x_m = Count_2 \\ CHO_1 * x_1 + CHO_2 * x_2 + ... + CHO_m * x_m = Count_3 \end{cases};$$

where $fat_m$ represents a fat content of a $m^{th}$ food, $x_m$ represents a mass of the $m^{th}$ food, $Count_1$ represents a fat mass required by the user for each meal in the candidate recipe, $protein_m$ represents a protein content of the $m^{th}$ food, $Count_2$ represents a protein mass required by the user for each meal in the candidate recipe, $CHO_m$ represents a carbohydrate content of the $m^{th}$ food, and $Count_3$ represents a carbohydrate mass required by the user for each meal in the candidate recipe; m is a quantity of food types in the target recommended recipe, and m is a positive integer.

In an exemplary embodiment of the present disclosure, the method further includes:
  presetting, based on a preset meal preparation rule of each meal, a constraint condition of each nutrient required by the user according to the basic information of the user; and
  determining the mass of each food in the target recommended recipe according to the constraint condition.

In an exemplary embodiment of the present disclosure, the method further includes:
  determining a content of each nutrient of each food in the target recommended recipe, and vectorizing the content of each nutrient of each food; and
  outputting the mass of each food in the target recommended recipe by using the vector of the content of each nutrient as an input of a neural network model.

In an exemplary embodiment of the present disclosure, a loss function of the neural network model is expressed as: Loss=$\|\sigma-\sigma'\|^2$+regular term,
where $\sigma$=($Count_1$, $Count_2$, $Count_3$), and the regular term is a preset constraint condition of each nutrient required by the user.

In an exemplary embodiment of the present disclosure, the method further includes:
  determining the multiple candidate foods according to a food knowledge graph and the basic information of the user.

In an exemplary embodiment of the present disclosure, the method further includes:
  obtaining the basic information of the user, wherein the basic information comprises at least one of age, gender, ethnicity, disease information, taste preference, and weight.

In an exemplary embodiment of the present disclosure, the method further includes:
  outputting at least one of the mass of each nutrient required by the user for each meal and the mass of each food in the target recommended recipe.

The present disclosure provides a diet recommendation device, including:
  a data obtaining module, configured to obtain historical dining data of a user; and a recipe determining module, configured to determine a target recommended recipe by using a recommendation model based on multiple candidate foods and the historical dining data.

In an exemplary embodiment of the present disclosure, the device further includes:
- a model constructing module, configured to construct a hierarchical graph model based on the multiple candidate foods; and
- a target recipe determining module, configured to determine, based on the historical dining data, the target recommended recipe by using the hierarchical graph model according to a random walk algorithm.

In an exemplary embodiment of the present disclosure, the model constructing module is configured to construct the hierarchical graph model by taking the multiple candidate foods as nodes, and paths between the nodes as edges.

In an exemplary embodiment of the present disclosure, the device further includes:
- a weight setting module, configured to initialize a weight of each edge in the hierarchical graph model;
- a weight updating module, configured to update the weight of each edge according to the historical dining data of the user; and
- a target recommended recipe determining module, configured to determine candidate foods contained in a path with a largest weight as the target recommended recipe.

In an exemplary embodiment of the present disclosure, the target recommended recipe determining module includes:
- a first probability value determining unit, configured to obtain, based on the weight of the path corresponding to the target recommended recipe, a probability of the user selecting the target recommended recipe as a first probability value;
- a second probability value determining unit, configured to obtain probabilities of multiple other users selecting the target recommended recipe as second probability values; and
- a target recipe probability determining unit, configured to determine a probability of the user selecting the target recommended recipe based on the first probability value and the second probability values.

In an exemplary embodiment of the present disclosure, the recipe determining module is further configured to determine the target recommended recipe by using an attention mechanism model based on the multiple candidate foods and the historical dining data.

In an exemplary embodiment of the present disclosure, the recipe determining module further includes:
- a meal preparation template setting module, configured to preset multiple templates for a meal preparation rule of each meal based on the multiple candidate foods;
- a template vectorizing module, configured to obtain multiple template vectors by vectorizing the multiple templates;
- an implicit vector obtaining module, configured to determine a food of each meal in the historical dining data of the user, and obtain an implicit vector of each meal by vectorizing the food and performing feature extraction on the food vector;
- a target template vector determining module, configured to determine, based on the attention mechanism model, a target template vector according to the implicit vector of each meal and the multiple template vectors;
- an enhanced vector obtaining module, configured to obtain an enhanced target template vector by performing an operation on the implicit vector of each meal with the target template vector; and
- a target recommended recipe determining module, configured to output the target recommended recipe corresponding to a target template in response to classifying the enhanced target template vector through a neural network classifier.

In an exemplary embodiment of the present disclosure, the implicit vector of each meal comprises a second vector and a third vector, and the implicit vector obtaining module includes:
- a first vector obtaining module, configured to determine the food of each meal in the historical dining data of the user, and obtain a first vector of each meal by vectorizing the food;
- a second vector obtaining module, configured to obtain the second vector of each meal by performing an operation on the first vector of each meal using a first parameter matrix; and
- a third vector obtaining module, configured to obtain the third vector of each meal by performing an operation on the first vector of each meal using a second parameter matrix.

In an exemplary embodiment of the present disclosure, the target template vector determining module includes:
- a sample information obtaining module, configured to obtain multiple sets of sample information, wherein each set of sample information comprises: the implicit vector of each meal and the multiple template vectors; and
- a model training module, configured to train the attention mechanism model by taking the implicit vector of each meal as an input, wherein probability values of the multiple template vectors are outputs, and determine a template vector with the largest probability value as the target template vector.

In an exemplary embodiment of the present disclosure, the enhanced vector obtaining module includes:
- an attention score calculating module, configured to calculate an attention score between the target template vector and the second vector of each meal; and
- a target template enhanced vector obtaining module, configured to obtain the enhanced target template vector by performing weighted average on the third vector of each meal according to the attention score corresponding to the implicit vector of each meal.

The present disclosure provides a computer-readable storage medium on which a computer program is stored, and the computer program, when executed by a processor, implements any one of the methods described above.

The present disclosure provides an electronic device, including: a processor; and a memory for storing executable instructions of the processor; where the processor is configured to execute any one of the methods described above by executing the executable instructions.

It should be noted that the above general description and the following detailed description are merely exemplary and explanatory and should not be construed as limiting of the disclosure.

BRIEF DESCRIPTION OF THE DRAWINGS

The accompanying drawings, which are incorporated in the specification and constitute a part of the specification, show exemplary embodiments of the present disclosure. The drawings along with the specification explain the principles of the present disclosure. It is apparent that the drawings in the following description show only some of the embodiments of the present disclosure, and other drawings may be obtained without creative effort by those skilled in the art according to the drawings described herein.

DETAILED DESCRIPTION

Figure 1:
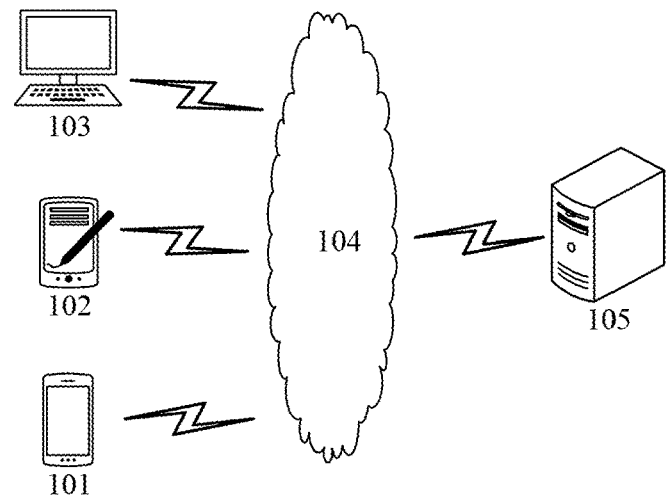
FIG. 1 shows a schematic diagram of an exemplary system architecture for a diet recommendation method and device that can be applied to the embodiments of the present disclosure.

Exemplary embodiments will now be described more fully with reference to the accompanying drawings. However, the embodiments can be implemented in a variety of forms and should not be construed as being limited to the examples set forth herein; rather, these embodiments are provided so that the present disclosure will be more complete to convey the idea of the exemplary embodiments to those skilled in this art. The described features, structures, or characteristics may be combined in one or more embodiments in any suitable manner. In the following description, many specific details are provided to fully understand the embodiments of the present disclosure. However, those skilled in the art will appreciate that the technical solution of the present disclosure may be practiced without one or more of the specific details, or other methods, components, devices, steps, and the like may be employed. In other instances, well-known technical solutions are not shown or described in detail to avoid obscuring various aspects of the present disclosure by overwhelming them.

In addition, the drawings are merely schematic representations of the present disclosure and are not necessarily drawn to scale. The same reference numerals in the drawings denote the same or similar parts, and the repeated description thereof will be omitted. Some of the block diagrams shown in the figures are functional entities and do not necessarily correspond to physically or logically separate entities. These functional entities may be implemented in software, or implemented in one or more hardware modules or integrated circuits, or implemented in different networks and/or processor devices and/or microcontroller devices.

FIG. 1 shows a schematic diagram of system architecture of an exemplary application environment in which a diet recommendation method and device of embodiments of the present disclosure can be applied.

As shown in FIG. 1, the system architecture 100 may include one or more of terminal devices 101, 102, and 103, a network 104 and a server 105. The network 104 is used to provide a medium for communication links between the terminal devices 101, 102, 103 and the server 105. The network 104 may include various connection types, such as wired, wireless communication links, or fiber optic cables, and so on. The terminal devices 101, 102, 103 may be various electronic devices, including but not limited to desktop computers, portable computers, smart phones, tablet computers, etc., and may also be various household appliances, such as smart refrigerators and smart range hoods. It should be understood that the numbers of terminal devices, networks, and servers in FIG. 1 are merely illustrative. According to implementation needs, there can be any number of terminal devices, networks, and servers. For example, the server 105 may be a server cluster composed of multiple servers.

The diet recommendation method provided by the embodiments of the present disclosure is generally executed by the server 105. Accordingly, the diet recommendation device is generally disposed in the server 105. After completing the diet recommendation, the server sends a recommendation result to the terminal device, and the terminal device can display it to the user. However, it is easily understood by those skilled in the art that the diet recommendation method provided by the embodiments of the present disclosure can also be executed by one or more of the terminal devices 101, 102, 103, and correspondingly, the diet recommendation device can also be disposed in the terminal devices 101, 102, and 103. For example, after completing the diet recommendation, the terminal device can directly display the recommendation result on a display screen of the terminal device, or the recommendation result can be provided to the user through voice broadcast, which is not specifically limited in this exemplary embodiment.

Figure 2:
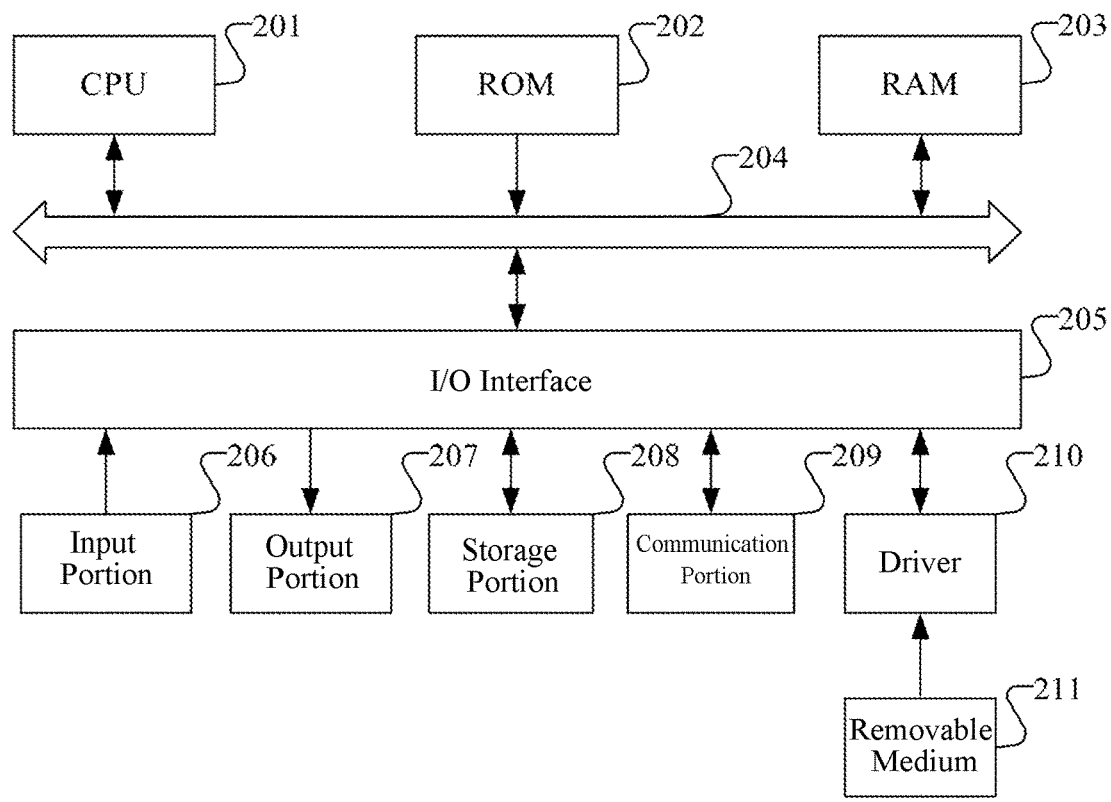
FIG. 2 shows a structural schematic diagram of a computer system suitable for implementing an electronic device of embodiments of the present disclosure.

FIG. 2 shows a schematic structural diagram of a computer system suitable for implementing an electronic device according to an embodiment of the present disclosure.

It should be noted that the computer system 200 of the electronic device shown in FIG. 2 is only an example, and should not bring any limitation to the functions and scope of use of the embodiments of the present disclosure.

As shown in FIG. 2, the computer system 200 includes a central processing unit (CPU) 201, which can execute a variety of appropriate actions and processes according to the program stored in a read-only memory (ROM) 202 or the program loaded from a storage portion 208 into a random access memory (RAM) 203. In RAM 203, there also store various programs and data required for the operation of the system. CPU 201, ROM 202, and RAM 203 are connected to one another via a bus 204. An input/output (I/O) interface 205 is also connected to the bus 204.

The following components are connected to the I/O interface 205: an input portion 206 including keyboard, mouse and etc.; an output portion 207 including cathode ray tube (CRT), liquid crystal display (LCD) and a speaker and etc.; a storage portion 208 including a hard disk and etc.; and a communication portion 209 including a network interface card such as LAN card, modem etc. The communication portion 209 performs communication processing over a network such as Internet. A driver 210 is also connected to the I/O interface 205 as needed. A removable medium 211, such as magnetic disc, optical disc, magneto optical disc, semiconductor memory, is installed on the driver 210 as needed, so that the computer program read from it is loaded into the storage portion 208 as needed.

In some embodiments, the diet recommendation method described in the present disclosure is executed by a processor of the electronic device. In some embodiments, information such as basic information of the user and historical dining data is input through the input portion 206, for example, the information such as the basic information of the user and the historical dining data is input through a user interactive interface of the electronic device. In some embodiments, information such as a target recommended recipe, a mass of each nutrient required by the user for each meal, and a mass of each food in the target recommended recipe is output through the output portion 207.

In particular, according to the embodiments of the present disclosure, the processes described below with reference to the flowcharts may be implemented as a computer software program. For example, the embodiments of the present disclosure include a computer program product including a computer program embodied on a computer-readable medium, the computer program containing program codes for performing the methods illustrated in the flowcharts. In such embodiment, the computer program may be downloaded and installed from the network through the communication portion 209, and/or installed from the removable medium 211. When the computer program is executed by the central processing unit (CPU) 201, the above-described functions defined in the method and device of the present disclosure are executed.

As another aspect, the present application also provides a computer-readable medium. The computer-readable medium may be included in the electronic device described in the above embodiments; or it may exist alone without being assembled into the electronic device. The computer-readable medium carries one or more programs, and the one or more programs, when executed by the electronic device, causes the electronic device to implement the method described in the following embodiments. For example, the electronic device can implement the steps shown in FIG. 3, FIG. 5, FIG. 7 to FIG. 8, and FIG. 10, etc.

It should be noted that the computer-readable medium shown in the present disclosure may be a computer-readable signal medium or a computer-readable storage medium or any combination thereof. The computer-readable storage medium may be, for example but not limited to, an electronic, magnetic, optical, electromagnetic, infrared, or semiconductor system, apparatus, or device, or any combination of the above. More specific examples of the computer-readable storage medium may include, but are not limited to, an electrical connection with one or more wires, a portable computer disk, a hard disk, a random access memory (RAM), a read-only memory (ROM), and an erasable programmable read-only memory (EPROM or flash memory), optical fiber, portable compact disk read-only memory (CD-ROM), optical storage device, magnetic storage device, or any suitable combination of the above. In the present disclosure, the computer-readable storage medium may be any tangible medium that contains or stores a program that can be used by or in conjunction with an instruction execution system, apparatus, or device. In the present disclosure, the computer-readable signal medium may include a data signal that propagates in baseband or as part of a carrier wave carrying computer-readable program codes. Such propagated data signals may have a variety of forms, including but not limited to electromagnetic signals, optical signals, or any suitable combination of the above. The computer-readable signal medium may also be any computer-readable medium other than a computer-readable storage medium that can transmit, communicate, or transport a program for use by or in connection with an instruction execution system, apparatus, or device. Program codes embodied on a computer readable medium may be transmitted using any suitable medium, including but not limited to wireless, wire, fiber optic cable, RF, etc., or any suitable combination of the above.

The technical solutions of the embodiments of the present disclosure are described in detail below.

A meal preparation method may be, for example, analyzing user's nutritional indicators based on the basic information of the user to give corresponding nutritional suggestions, and recommend a recipe that meets nutritional needs. However, this method does not refer to user's dining preferences, resulting in low accuracy of the recommended recipe. In addition, there are certain limitations in the way of determining the user's preference only based on the user's dining history.

Figure 3:
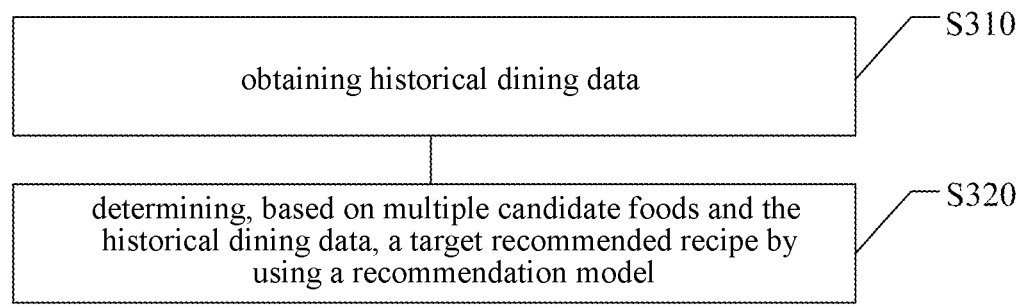
FIG. 3 schematically shows a flowchart of a diet recommendation method according to an embodiment of the present disclosure.

Based on one or more of the above problems, this exemplary embodiment provides a diet recommendation method. The method can be applied to the server 105, and can also be applied to one or more of the terminal devices 101, 102, 103, which is not particularly limited in the exemplary embodiment. Referring to FIG. 3, the diet recommendation method may include the following steps S310 to S320.

In a step S310, historical dining data is obtained.

In a step S320, a target recommended recipe is determined by using a recommendation model based on multiple candidate foods and the historical dining data.

In the diet recommendation method provided by the exemplary embodiment of the present disclosure, by obtaining the historical dining data of the user, the target recommended recipe is determined by using the recommendation model based on the multiple candidate foods and the historical dining data. The method can accurately determine the user's favorite recipe through the recommendation model, and can recommend a scientific and reasonable recipe for the user by calculating the mass of each food in the recipe.

Hereinafter, the above steps of the exemplary embodiment will be described in more detail.

In the step S310, the historical dining data is obtained.

In this exemplary embodiment, the historical dining data of the user can be obtained every time it is used, or can be obtained according to a preset time period. For example, the historical dining data of the user is obtained once every month, and the food is recommended based on the latest historical dining data of the user. The historical dining data of the user may refer to the food selected by the user for each meal recently (last few days, months, etc. without limitation on time). The food may include staple food, soup, porridge, dish, and other types, and the staple food can include rice, steamed bread and so on, the soup may include tomato and egg soup, seaweed and egg soup, and the like, the porridge may include rice porridge, pumpkin porridge and the like, and the dish can include scrambled eggs with tomatoes, fried cabbage and so on.

Exemplarily, the food selected by the user for three meals per day in the past month can be obtained. For example, the breakfast on the first day is steamed bread, rice porridge and fried cabbage, and lunch and dinner are similar. It is also possible to obtain the food selected by the user for each meal in the past 15 days and 20 days, which is not limited in this exemplary embodiment.

For example, the basic information of the user can also be obtained, and the basic information of the user can be the user's age, gender, ethnicity, disease information, taste preference, weight, etc. After the basic information of the user is obtained, the multiple candidate foods can be determined according to a food knowledge graph and the basic information of the user.

The knowledge graph is a graph-based data structure composed of nodes and edges. In the knowledge graph, the node represents an entity or a concept, and the edge is composed of attributes or relationships. The knowledge graph is the most effective way to express the relationships, which refers to a relational network obtained by connecting all different types of information together. Therefore, the knowledge graph provides the ability to analyze problems from a "relationship" perspective.

Figure 4:
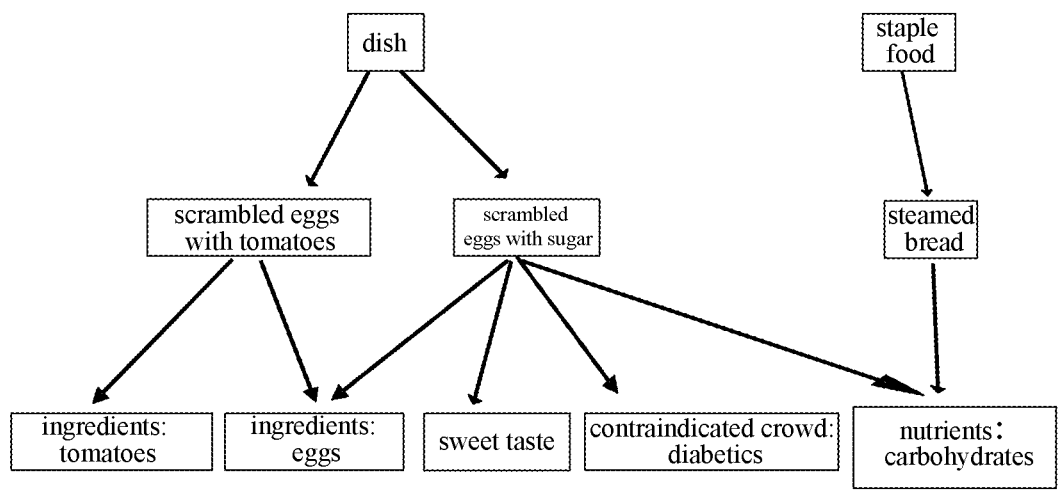
FIG. 4 schematically shows a schematic diagram of a food knowledge graph according to an embodiment of the present disclosure.

In this exemplary embodiment, the food knowledge graph can be constructed. The entities of the food knowledge graph can be various types of foods, and the attributes of the entities can include information such as nutrient components, tastes, effects of food materials, and contraindicated crowd of food. As shown in FIG. 4, the food entities in the food knowledge graph include scrambled eggs with tomatoes, scrambled eggs with sugar, and steamed bread. The attributes of scrambled eggs with tomatoes can include ingredients such as tomatoes and eggs. The attributes of scrambled eggs with sugar can include sweet taste, ingredients such as eggs, the contraindicated crowd being diabetics, and the nutrient content including carbohydrates. The attributes of steamed bread can include carbohydrates and so on. In addition, the food knowledge graphs are separately constructed for the dish and the staple food, or the dish and the staple food can be simultaneously reflected in the same knowledge graph.

The constructed food knowledge graph can be stored for subsequent access and calling. Therefore, the food knowledge graph can be constructed in real time every time a food recommendation is made for the user, or it can be pre-built and stored in the database. For example, the food knowledge graph can be stored in Neo4j database (a high-performance NoSQL graph database), which can be called when the food recommendation is made for the user.

In some embodiments, the multiple candidate foods may be determined according to the food knowledge graph and the basic information of the user. For example, if the user's ethnicity is the Hui nationality, the food attributes can be searched in the food knowledge graph, and relevant food such as pork that is not suitable for the Hui nationality users can be discarded. For example, for diabetic patients, the daily sugar intake and intake requirements of monosaccharide and polysaccharide for diabetic users can be determined according to medical food prohibition rules or doctor's advices, etc., and whether the food is a high-glycemic food or whether it is in compliance with the food prohibition rules or doctor's advices can be determined according to the food knowledge graph. The food that does not meet the conditions are discarded, and the remaining food (not discarded) in the food knowledge graph is used as the candidate food. A query language such as Cypher can be used to search and query in the knowledge graph, in order to find the multiple candidate foods that meet the basic information of the user. The candidate food may be steamed bread, rice porridge, scrambled eggs with tomatoes and the like. It is also possible to use the food contained in each meal in the historical dining data of the user as the candidate food. The candidate food is screened based on the basic information of the user, which can provide the user with more accurate recipes and improve the user experience. It is also possible to arrange the multiple candidate foods based on the historical dining data of the user through a binary sort tree, and determine the multiple candidate foods according to the basic information of the user. The candidate multiple foods can also be determined by creating relational data, for example, creating a My SQL database, which is not limited by this embodiment.

In some embodiments, a meal preparation rule of each meal can be preset. For example, in order to combine various foods reasonably, the food for breakfast can be preset, which can include staple food, drink, and dish, or include staple food, and dish, or include staple food, drink, dish and dessert, and the lunch and dinner are similar. It is understandable that the meal preparation rule of each meal can be set according to the actual needs of the user. For example, the user can input the meal preparation rule through a user interactive interface of the terminal or the like. Alternatively, the meal preparation rule can be uniformly preset in the background. For example, the multiple candidate foods are combined and matched according to the meal preparation rule and then recommended to the user, which is not limited in this exemplary embodiment.

In the step S320, the target recommended recipe is determined by using the recommendation model based on the multiple candidate foods and the historical dining data.

Figure 5:
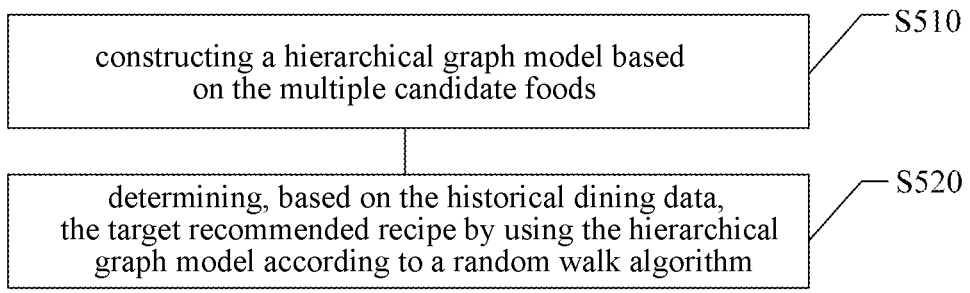
FIG. 5 schematically shows a flowchart of steps of determining a target recommended recipe according to an embodiment of the present disclosure.

In an exemplary embodiment, referring to FIG. 5, the process may include the following steps.

In a step S510, a hierarchical graph model is constructed based on the multiple candidate foods.

The multiple candidate foods can include steamed bread, rice porridge, scrambled eggs with tomatoes, etc. The foods such as steamed bread, rice porridge, scrambled eggs with tomatoes can be used as nodes respectively. Correspondingly, paths between the nodes are used as edges to construct the hierarchical graph model. The hierarchical graph model refers to the use of a "directed tree" data structure to represent various entities and relationships. Each node in the tree represents a recorded type, and the edge between nodes represents the relationship between the recorded types. The structure of the hierarchical graph model is clear, the relationship between nodes is simple, and the relationship between the recorded types is represented by a directed edge. Therefore, the efficiency of querying the candidate food according to the hierarchical graph model is high.

In a step S520, the target recommended recipe is determined, based on the historical dining data, by using the hierarchical graph mode according to a random walk algorithm.

The random walk algorithm refers to traversing the entire hierarchical graph model starting from a vertex or a series of vertices. At any vertex, a traversal will traverse to an adjacent vertex of this vertex with probability 1−a, and randomly jump to any vertex in the hierarchical graph model with probability a, where "a" is called a probability of jump occurrence. A probability distribution is derived after every travel, which describes a probability of each vertex in the hierarchical graph model being accessed. The probability distribution is used as the input of the next travel, which is iteratively performed. When an iteration termination condition is met, the probability distribution tends to converge. The iteration termination condition can be that the preset number of iterations is satisfied, for example, the probability distribution tends to converge after 100 iterations, or it can be other iteration termination conditions, for example, the iteration is performed until the probability distribution converges. After convergence, a stable probability distribution can be obtained.

Figure 6:
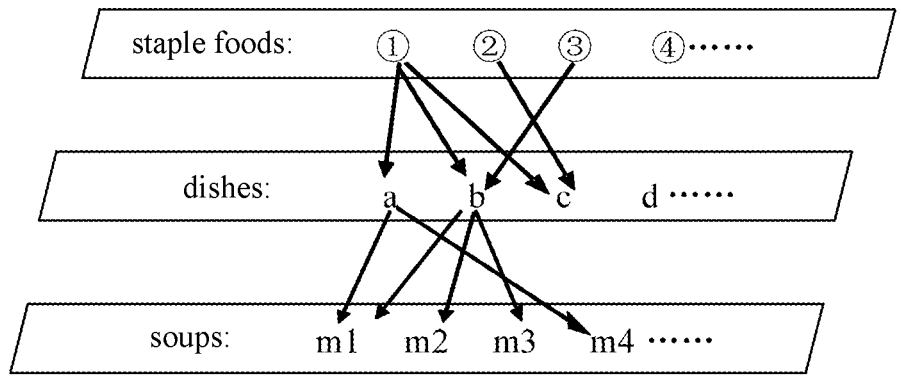
FIG. 6 schematically shows a schematic diagram of a hierarchical graph model according to an embodiment of the present disclosure.
Figure 7:
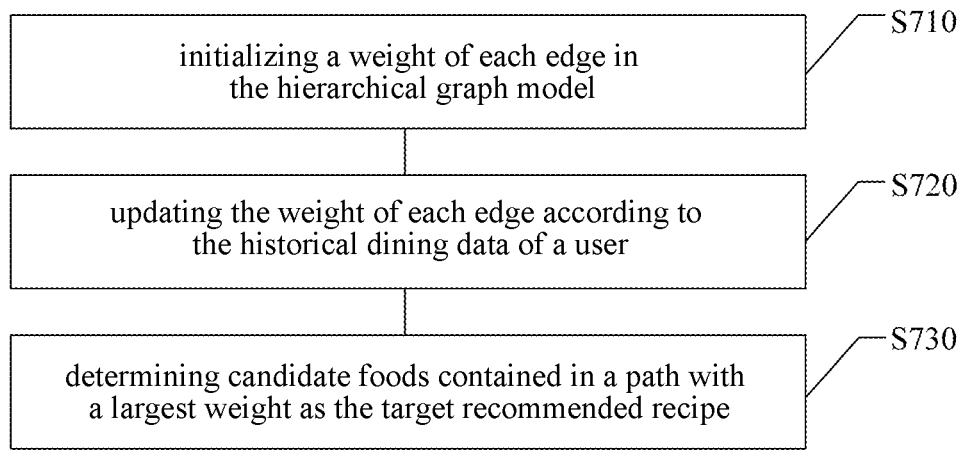
FIG. 7 schematically shows a flowchart of steps of determining a target recommended recipe according to a specific embodiment of the present disclosure.

Referring to the hierarchical graph model shown in FIG. 6, it is constructed with the multiple candidate foods as nodes and the paths between respective candidate foods as edges. The multiple candidate foods include staple foods ①, ②, ③, ④, etc., dishes a, b, c, d, etc., soups $m_1$, $m_2$, $m_3$, $m_4$, etc. The target recommended recipe can be determined through the hierarchical graph model. With reference to FIG. 7, the process can include the following steps.

In a step S710, a weight of each edge in the hierarchical graph model is initialized.

The weight of each edge in the hierarchical graph model can be initialized. For example, an initial weight of each edge in the hierarchical graph model can be set to 0, and the initial weight of each edge can also be set to any other value. The purpose of setting the initial weight of each edge to 0 is to facilitate statistics of the weight change of each edge in the subsequent hierarchical graph model.

In a step S720, the weight of each edge is updated according to the historical dining data of the user.

The historical dining data of the user can be obtained, and the weight of each edge can be updated according to the historical dining data of the user. For example, the historical dining data of the user shows that the user's historical choices include: ①→b→$m_1$, ①→b, ①→a→$m_1$, ②→c and other paths. Assuming that for the path with node ① as the starting node there are ①→b→$m_1$, ①→b, ①→a→$m_1$, the weight of path ①→b is the number of the path (①→b)/(the number of paths including ①), which is ⅔. It can be seen that the path ①→b can be updated from the initial weight of 0 to ⅔ according to the historical dining data of the user.

In a step S730, a candidate food contained in a path with the largest weight is determined as the target recommended recipe.

After the weight of each edge is updated according to the historical dining data of the user, the weight of each path can be obtained. For example, the weight of path ①→b is ⅔, the weight of path ①→a is ⅙, the weight of path ①→c is ⅙, the weight of path b→$m_1$ is ⅓, and the weight of path b→$m_2$ is ⅓, and the weight of path b→$m_3$ is ⅓. When the food is recommended for the user, the path with a larger weight can be selected for recommendation, for example, the path ①→b (staple food① and dish b) can be selected, or the path ①→b→$m_1$ (staple food①, dish b and soup $m_1$) can also be selected. The larger weight means that the user has a greater probability of selecting the corresponding combination of the candidate foods, that is, a recipe composed of the combination of the candidate foods can be used as the target recommended recipe.

In this way, not only is it determined that the user is most interested in the recipe based on the user's historical selection behavior for the single combination ①→b, but also other recipes containing such a combination (such as ①→b→m2) are considered, the considered information is more comprehensive, and the recommendation is more accurate. In this case, it can be considered that the collocation of ①→b with other ingredients is also easier to be accepted by the user.

In some embodiments, a probability that the user selects the target recommended recipe can be obtained according to the weight of the path corresponding to the target recommended recipe, which is recorded as a first probability value $P_1$. According to big data statistical analysis, probabilities of multiple other users choosing the target recommended recipe can be obtained (for example, obtaining the probability of each of the multiple other users making a recipe recommendation based on the path, respectively, and taking the average value), which is recorded as second probability values $P_2$. Based on $P_1$ and $P_2$, the probability that the user will finally select the target recommended recipe can be obtained according to the formula $P=\alpha P_1+(1-\alpha)P_2$, where $\alpha$ refers to a weight of an event that the selection of the target recommended recipe is determined based on the historical dining data of the user, and correspondingly, $(1-\alpha)$ refers to a weight of an event that the selection of the target recommended recipe is determined based on choices of other users. Then, the P values of multiple target recommended recipes can be sorted, for example, in descending order, the top-ranked target recommended recipes are recommended to the user, for example, the target recommended recipes corresponding to the top ten P values after sorting are recommended to the user.

It can be seen that, based on the hierarchical graph model, by analyzing the historical dining data of the user to determine which food combination the user prefers, it is possible to recommend the recipe to the user more accurately. Moreover, by disassembling the foods in the food combination and matching with other candidate food, the user's favorite recipe is further optimized, providing the user with more choices, which can improve user experience and increase user stickiness.

Figure 8:
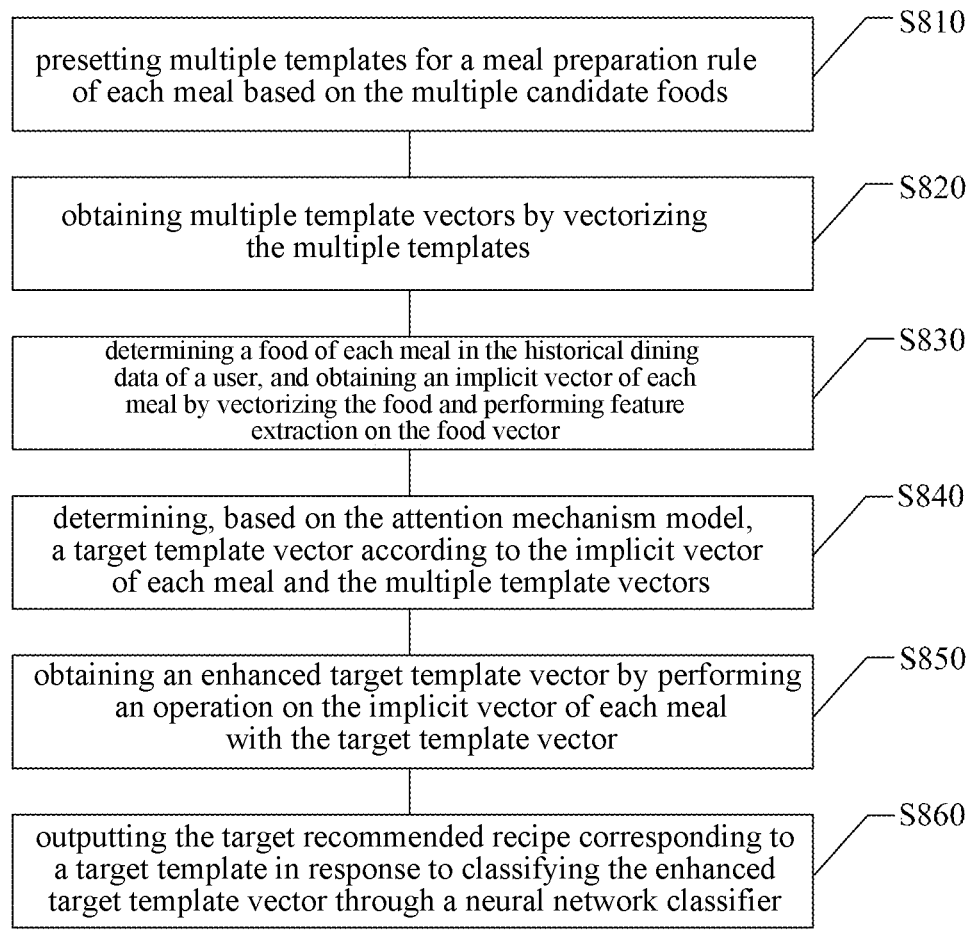
FIG. 8 schematically shows a flowchart of steps of determining a target recommended recipe according to another embodiment of the present disclosure.

In another exemplary embodiment, it is also possible to determine the target recommended recipe based on the multiple candidate foods and the historical dining data, using an attention mechanism model. With reference to FIG. 8, the process may include the following steps.

In a step S810, multiple templates are preset for a meal preparation rule of each meal based on the multiple candidate foods.

The multiple templates can be preset for the meal preparation rule of each meal. For example, a template of the meal preparation rule of the breakfast may include staple food, porridge, dish, or staple food, porridge, soup, or food, dish, dessert, and so forth. The lunch and dinner are similar. The number of templates for meal preparation is not limited in this exemplary embodiment.

In a step S820, multiple template vectors are obtained by vectorizing the multiple templates.

In some embodiments, each item in each template may be encoded by One-Hot encoding to obtain a One-Hot encoding vector, that is, a template vector. The One-Hot encoding, also known as one-bit effective encoding, is done by using N-bit state register to encode N states, each with a separate register bit, and at any time, only one bit in the register is valid. Dimensions of each template vector are the number of types of all candidate foods. Each template can also be converted into a vector through a Word Embedding algorithm, such as a Word2vec algorithm, a Glove algorithm, etc. Alternatively, each template can also be converted into a vector through other methods, such as algorithms like TransE.

In a step S830, food of each meal in the historical dining data of the user is determined, and an implicit vector of each meal is obtained by vectorizing the food and performing feature extraction on the food vector.

Exemplarily, the historical dining data of the user is obtained, each meal can contain the multiple candidate foods, and each candidate food can be coded through the attention mechanism model, and then each candidate food can be vectorized. The attention mechanism model is a machine learning model that simulates human visual attention behavior. When a human is observing a picture, after scanning the image globally, he will get a target area that needs attention, and then put more attention on it, so as to obtain the detailed information of the target area. Therefore, the human attention behavior can be abstracted and applied to the machine learning model. The attention mechanism model may include: an embedding layer, a neural network layer, an attention layer, a connection layer, and a normalization layer.

In some embodiments, at the embedding layer of the attention mechanism model, each candidate food can be One-Hot encoded to obtain the vector of each meal, or each candidate food can also be converted into a vector through a Word Embedding algorithm, such as a Word2vec algorithm, a Glove algorithm, etc., or by other means, such as TransE algorithm.

Figure 9:
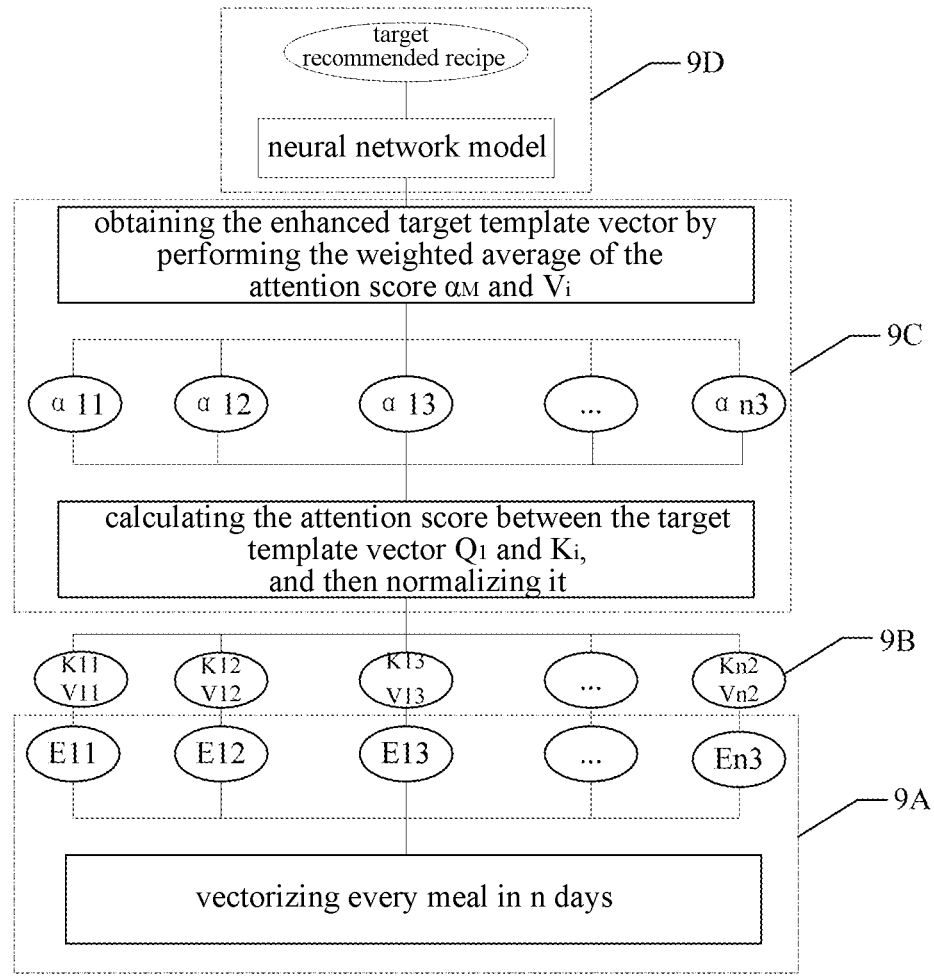
FIG. 9 schematically shows a flowchart of steps of determining a target recommended recipe according to another embodiment of the present disclosure.

For example, referring to part 9A in FIG. 9, the foods selected by the user for three meals a day in the past n days can be obtained, and each food can be used as the candidate food and vectorized to obtain $E_{11}$ for breakfast, $E_{12}$ for lunch, and $E_{13}$ for dinner on the first day . . . and $E_{n3}$ for dinner on the $n^{th}$ day.

The matrix composed of the vector of each meal can also be transformed into a dense matrix through linear transformation at the embedding layer of the attention mechanism model, that is, the high-dimensional sparse and irrelevant vector of each meal is projected to the low-dimensional vector.

In some embodiments, the implicit feature extraction can be performed on the low-dimensional vector of each meal through the neural network layer. For example, the implicit features can be extracted through a long and short-term memory network to obtain the implicit vector of each meal, and the implicit vector of each meal can include the second vector and the third vector. The long and short-term memory network is a time recursive neural network, which is suitable for processing and predicting important events with relatively long intervals and delays in time series. Of course, the implicit features can also be extracted through a convolutional neural network, a recurrent neural network, or other networks, which are not limited here.

Exemplarily, the food in each meal in the historical dining data of the user may be vectorized to obtain a first vector of each meal. An operation is performed on the first vector of each meal through a first neural network layer of the attention mechanism model to obtain the second vector of each meal. The operation is performed on the first vector of each meal through a second neural network layer of the attention mechanism model to obtain the third vector of each meal.

In some embodiments, the first vector can also be directly operated with each parameter matrix to obtain the second vector and the third vector.

For example, referring to part 9B in FIG. 9, the first vector of each meal can be multiplied by a first parameter matrix $W_1$ to obtain $K_{11}=W_1*E_{11}$, $K_{12}=W_1*E_{12}$ . . . , $K_{n3}=W_1*E_{n3}$, where $K_{11}$, $K_{12}$ are respectively the second vectors of each meal.

The first vector of each meal can be multiplied by a second parameter matrix $W_2$ to obtain $V_{11}=W_2*E_{11}$, $V_{12}=W_2*E_{12}$ . . . , $V_{n3}=W_2*E_{n3}$, where $V_{11}$, $V_{12}$ are respectively the third vectors of each meal.

The target template vector is determined during the training process of the model. The specific process is as follows.

The target template vector is determined according to the implicit vector of each meal and the multiple template vectors based on the attention mechanism model.

The machine learning model is trained based on a large amount of sample information, and the target template can be determined after the attention mechanism model is trained. During the training process, multiple sets of sample information may be obtained first, and each set of sample information includes: a template vector, an implicit vector of each meal corresponding to the historical dining data of the user, and a corresponding probability of the user selecting the sample template vector. The attention mechanism model is trained by taking the implicit vector of each meal as an input, and probability values of the multiple template vectors as outputs, and a template vector with the largest probability value is used as the target template vector, which is denoted as $Q_1$.

In this exemplary embodiment, the process of training the attention mechanism model is a process of continuously updating the parameters in the model. A loss function can be calculated according to a probability of the user selecting the sample template vector and a predicted probability, and the attention mechanism model can be updated according to the loss function. The parameters $u^T$, $W_h$ and $W_s$) in the attention mechanism model are preset. During the training process, the loss function can be continuously calculated according to a back propagation principle by using a gradient descent method, and the parameters in the model can be updated according to the loss function. After the parameters corresponding to each set of samples are determined, the target template is determined according to the output probability of each set of sample template vectors.

In a step S840, an enhanced target template vector is obtained by performing an operation on the implicit vector of each meal with the target template vector.

For the target template vector, an attention score between the target template vector and the implicit vector of each meal can be calculated through the attention layer of the attention mechanism model. The attention score is a value in the range from 0 to 1, and the sum of all attention scores under the action of the attention mechanism model is 1. Each attention score represents an attention weight assigned to the current item. The attention score is often learned from the weight parameter of the neural network in the training of the model, and finally normalized.

In an exemplary embodiment, the attention score between the target template vector $Q_1$ and the second vector $K_i$ of each meal can be calculated by using a dot product model in the attention scoring function, that is, a similarity between the target template vector and the second vector can be calculated. For example, the similarity between these two vectors can be obtained by calculating the dot product of $K_i$ and $Q_1$, that is, $\alpha_i=K_i \cdot Q_1$. According to the similarity $\alpha_i$ between the target template vector and the second vector, the third vector $V_i$ of each meal is performed by a weighted average, that is, $c_1=\Sigma_1^M a_i \times V_i$, so as to obtain the enhanced target template vector, where i is an integer from 1 to M, and M represents the number of all meals in n days.

In an exemplary embodiment, the attention score $f(h_i, s)$ can also be calculated through an additive model in the attention scoring function, that is, according to the formula $f(K_i, Q_1)=u^T \tan h(W_h*K_i+W_s*Q_1)$, where $K_i$ represents the implicit vector of the $i^{th}$ meal, i is an integer from 1 to M, M represents the number of all meals in n days, $Q_1$ represents the target template vector, $u^T$, $W_h$ and $W_s$ represent the parameters of the attention mechanism model, $$\tanh(x) = \frac{e^x - e^{-x}}{e^x + e^{-x}}.$$

For example, referring to part 9C in FIG. 9, the attention score $f(K_i, Q_1)$ between the target template vector $Q_1$ and the second vector $K_i$ of each meal can be calculated according to the above formula. Individual attention scores $f(K_i, Q_1)$ can be normalized to obtain weights $\alpha_1, \ldots, \alpha_M$, and then the weighted average is performed with the third vector $V_i$ of each meal to obtain the enhanced vector $c_1$, that is, $c_1 = \Sigma_1^M \alpha_i \times V_i$.

In an exemplary embodiment, the attention score can also be calculated according to the zoom click model and the bilinear model in the attention scoring function.

In a step S850, the target recommended recipe corresponding to the target template is output in response to classifying the enhanced target template vector through a neural network classifier.

As shown in part 9D in FIG. 9, the enhanced target template vector can be classified by the neural network classifier. For example, the target recommended recipe corresponding to the target template can also be output through pooling processing and normalization operation. It can be seen that in this exemplary embodiment, the enhanced target template vector, that is, an important feature vector, is extracted through the attention mechanism model, and the important feature vector is matched with multiple candidate recipes in the database, so that the corresponding target recommended recipe can be matched more accurately.

In the above recommendation method based on the attention mechanism model, the user's favorite recipe template and the recipe determined according to the template can be obtained at the same time, and the recommendation can be made according to preset template rules.

Figure 10:
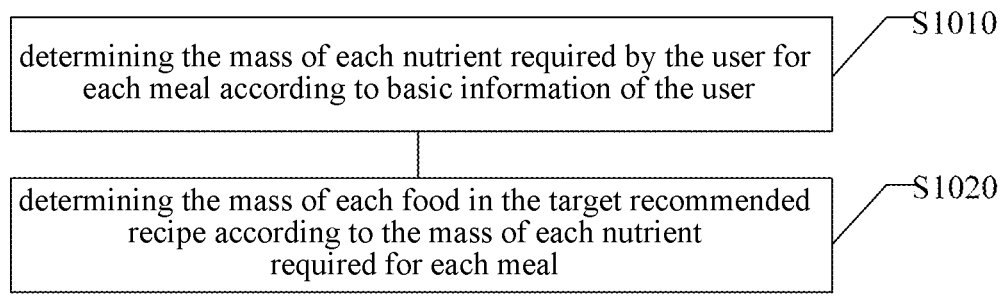
FIG. 10 schematically shows a flowchart of steps of determining a mass of each food in a target recommended recipe according to an embodiment of the present disclosure.

In an exemplary embodiment, a mass of each food in the target recommended recipe can also be determined according to a mass of each nutrient required for each meal. Referring to FIG. 10, the process may include the following steps.

In a step S1010, the mass of each nutrient required by the user for each meal is determined according to basic information of the user.

In some embodiments, the basic information of the user is obtained through a user interactive interface. For example, the user inputs at least one of age, gender, ethnicity, disease information, taste preference, and weight through the user interactive interface.

In this exemplary embodiment, the energy required by the user for each meal can be determined according to the basic information of the user first, and then the mass of each nutrient required by the user for each meal can be determined according to a relationship between the energy required by the user for each meal and each nutrient.

Specifically, based on nutrition rules, a reasonable range of the total energy required by the user in a day can be obtained according to the basic information of the user. For example, the energy allocation for breakfast, lunch, and dinner in a day can be determined by nutritional data, or the energy required for each meal can be allocated according to the actual needs of the user, such as breakfast accounting for 35%, lunch accounting for 40%, and dinner accounting for 25%, and the range of energy the user should consume for each of the three meals can be determined. For example, if the total energy required by the user in a day is 1000 calories, then 350 calories are needed for breakfast, 400 calories for lunch, and 250 calories for dinner.

The mass of each nutrient required by the user for each meal can be determined according to the relationship between the energy required by the user for each meal and each nutrient, that is, $$\begin{cases} nutrientCount_1 = energy * ratio_1 / param_1 \\ nutrientCount_2 = energy * ratio_2 / param_2 \\ \ldots \\ nutrientCount_n = energy * ratio_n / param_n \end{cases};$$

Here, $nutrientCount_n$ represents a mass of the $n^{th}$ nutrient; energy represents an energy value required by the user for each meal in a candidate recipe; $ratio_n$ represents a ratio coefficient of the $n^{th}$ nutrient to the energy value of each meal; and $param_n$ represents a converted energy coefficient of the $n^{th}$ nutrient; and n is a positive integer.

In a step S1020, the mass of each food in the target recommended recipe is determined according to the mass of each nutrient required for each meal.

In an exemplary embodiment, the mass of each food in the target recommended recipe is determined according to the relationship between a content of each nutrient in a candidate food contained in the target recommended recipe and the mass of each nutrient required for each meal, that is, according to:

$$\begin{cases} fat_1 * x_1 + fat_2 * x_2 + \ldots + fat_m * x_m = Count_1 \\ protein_1 * x_1 + protein_2 * x_2 + \ldots + protein_m * x_m = Count_2 \\ CHO_1 * x_1 + CHO_2 * x_2 + \ldots + CHO_m * x_m = Count_3 \end{cases}$$

Here, $fat_m$ represents a fat content of the $m^{th}$ food, $x_m$ represents a mass of the $m^{th}$ food, $Count_1$ represents a fat mass required by the user for each meal in the candidate recipe, $protein_m$ represents a protein content of the $m^{th}$ food, $Count_2$ represents a protein mass required by the user for each meal in the candidate recipe, $CHO_m$ represents a carbohydrate content of the $m^{th}$ food, $Count_3$ represents a carbohydrate mass required by the user for each meal in the candidate recipe; m is the number of food types in the target recommended recipe, and m is a positive integer.

For example, the target recommended recipe consists of bread, milk, and fried cabbage, then m=3 in the above formula, and the above equation group has a unique solution, that is, the mass of each food in the target recommended recipe can be determined, which can improve the accuracy of the recommended recipe to meet the needs of the user.

For another example, if the target recommended recipe consists of rice, lemon juice, fried cabbage, and cake, then m=4 in the above formula, and the above equation set may have more than one solution, that is, there are multiple ways for distributing the food mass in a certain candidate recipe, and the mass of each food in the target recommended recipe cannot be determined. Therefore, based on the preset meal preparation rule of each meal, the constraint condition of each nutrient required by the user can also be preset according to the basic information of the user. For example, for diabetic patients, the intake of carbohydrates can be controlled within a reasonable range, and the corresponding constraint condition on the intake of carbohydrates can be: $c_1*x_1+c_2*x_2+\ldots+c_m*x_m \leq \text{Count}_4$, where $c_m$ represents the sugar content of the $m^{th}$ food, $x_m$ represents the mass of the $m^{th}$ food, and $\text{Count}_4$ represents the sugar mass required by the user for each meal in the target recommended recipe. Based on the above formula and then according to the constraint condition, the mass of each food in the target recommended recipe can be determined, so as to provide the user with a more suitable recipe to meet the needs of the user.

In an exemplary embodiment, when the mass of each food in the target recommended recipe is determined according to the relationship between a content of each nutrient in a candidate food contained in the target recommended recipe and the mass of each nutrient required for each meal, it is also possible to determine the mass of each food in the target recommended recipe based on:

$$\begin{cases} \text{fat}_1*x_1 + \text{fat}_2*x_2 + \ldots + \text{fat}_m*x_m = f_x \\ \text{protein}_1*x_2 + \text{protein}_2*x_2 + \ldots + \text{protein}_m*x_m = p_x \\ \text{CHO}_1*x_1 + \text{CHO}_2*x_2 + \ldots + \text{CHO}_m*x_m = C_x \end{cases}$$

Here, each group $(x_1, x_2, \ldots x_m)$ corresponds to a group $(f_x, p_x, C_x)$, and $f_x, p_x, C_x$ are the actual calculated nutrient mass required for each meal.

In order to determine the mass of each food in the target recommended recipe $x_1, x_2 \ldots x_m$, a constraint function can be set as:

$$\Phi = \min((f(x) - \text{Count}_1)^2 + (p(x) - \text{Count}_2)^2 + (p(x) - \text{Count}_3)^2 + |x_1| + |x_2| + \ldots + |x_m|)$$

Here, $\text{Count}_1, \text{Count}_2, \text{Count}_3$ are standard values of the mass of respective nutrients required by the user for each meal calculated according to the relationship between the energy required by the user for each meal and each nutrient. When the value of the above constraint function is the minimum value, the actual values $f_x, p_x, C_x$ of the mass of respective nutrients required by the user for each meal corresponding to the minimum value can be determined, and the mass of each food in the target recommended recipe corresponding to the minimum value can be determined.

In an exemplary embodiment, a content of each nutrient of each food in the target recommended recipe may be determined through step S910, and the content of each nutrient of each food is vectorized. Similarly, One-Hot encoding for the content of each nutrient can be performed, and the content of each nutrient can be vectorized to obtain the content vector of each nutrient.

Correspondingly, it is also possible to obtain multiple sets of sample data to train the neural network model first, and each set of sample data includes: the sample content vector of each nutrient, and the mass of each food in the target recommended recipe. The neural network model is trained by taking the sample content vector of each nutrient as an input, and taking the mass of each food in the target recommended recipe as an output.

Specifically, the content vector of each nutrient may be used as the input of the neural network model, and the neural network model is updated according to a loss function to output the mass of each food in the target recommended recipe. Similarly, the loss function can be continuously calculated according to a back propagation principle by using a gradient descent method, and the parameters in the neural network model can be updated according to the loss function.

The loss function of the neural network model can be Loss=$\|\sigma-\sigma'\|^2$+regular term, where $\sigma=(\text{Count}_1, \text{Count}_2, \text{Count}_3)$ includes the mass of each nutrient required by the user for each meal, $\sigma'$ represents the mass of each nutrient required by the user for each meal predicted by the neural network, and the regular term is a preset constraint condition of each nutrient required by the user. The loss function can be used to estimate the degree of inconsistency between the predicted value of the model and the true value. The loss function can also be an exponential loss function or a perceptual loss function, which is not limited in this exemplary embodiment. After the target recommended recipe is determined, it can be sent by the server to the user terminal for display. If the currently displayed target recommended recipe does not meet the user's preferences and needs, the user can switch to the next target recommended recipe, and all the target recommended recipes are recommended one by one.

In some embodiments, at least one of the total mass of each nutrient required by the user every day, the mass of each nutrient required for each meal, the mass of each food in the target recommended recipe, and the target recommended recipe may also be output. For example, the above information is output through the user interactive interface. For example, the user can edit various contents through the interface and adjust them according to personal needs.

In the diet recommendation method provided by the exemplary embodiments of the present disclosure, by obtaining the historical dining data of the user, the target recommended recipe is determined by using the recommendation model based on the multiple candidate foods and the historical dining data. And then the mass of each food in the target recommended recipe is determined according to the mass of each nutrient required for each meal. The method can accurately determine the user's favorite recipe through the recommendation model, and by calculating the mass of each food in the recipe, the scientific and reasonable recipe can be recommended for the user.

It should be noted that although the various steps of the method of the present disclosure are described in a particular order in the figures, this is not required or implied that the steps must be performed in the specific order, or all the steps shown must be performed to achieve the desired result. Additionally or alternatively, certain steps may be omitted, multiple steps may be combined into one step, and/or one step may be decomposed into multiple steps and so on.

Figure 11:
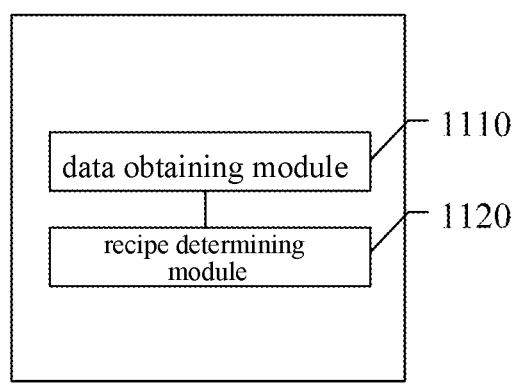
FIG. 11 schematically shows a block diagram of a diet recommendation device according to an embodiment of the present disclosure.

Further, in this exemplary embodiment, there is also provided a diet recommendation device. The device can be applied to a server or terminal device. Referring to FIG. 11, the diet recommendation device 1100 may include a data obtaining module 1110 and a recipe determining module 1120.

The data obtaining module 1110 is configured to obtain historical dining data of a user.

The recipe determining module 1120 is configured to determine a target recommended recipe by using a recommendation model based on multiple candidate foods and the historical dining data.

In some embodiments, the data obtaining module obtains the historical dining data of the user through the user interactive interface, for example, the user inputs the personal historical dining data through the user interactive interface.

In some embodiments, the target recommended recipe determined by the recipe determining module may be displayed to the user through the user interactive interface. In an optional embodiment, the recipe determining module 1120 includes:

a model constructing module, configured to construct a hierarchical graph model based on the multiple candidate foods; and a target recipe determining module, configured to determine, based on the historical dining data, the target recommended recipe by using the hierarchical graph model according to a random walk algorithm.

In an optional embodiment, the model constructing module is configured to construct the hierarchical graph model by taking the multiple candidate foods as nodes, and paths between the nodes as edges.

In an optional embodiment, the recipe determining module includes:

a weight setting module, configured to initialize a weight of each edge in the hierarchical graph model;

a weight updating module, configured to update the weight of each edge according to the historical dining data of the user; and a target recommended recipe determining module, configured to determine candidate foods contained in a path with a largest weight as the target recommended recipe.

In an optional embodiment, the target recommended recipe determining module includes:

a first probability value determining unit, configured to obtain, based on the weight of the path corresponding to the target recommended recipe, a probability of the user selecting the target recommended recipe as a first probability value;

a second probability value determining unit, configured to obtain probabilities of multiple other users selecting the target recommended recipe as second probability values; and a target recipe probability determining unit, configured to determine a probability of the user selecting the target recommended recipe based on the first probability value and the second probability values.

In an optional embodiment, the recipe determining module 1120 is further configured to determine the target recommended recipe by using an attention mechanism model based on the multiple candidate foods and the historical dining data.

In an optional embodiment, the recipe determining module 1120 further includes:

a meal preparation template setting module, configured to preset multiple templates for a meal preparation rule of each meal based on the multiple candidate foods;

a template vectorizing module, configured to obtain multiple template vectors by vectorizing the multiple templates;

an implicit vector obtaining module, configured to determine a food of each meal in the historical dining data of the user, and obtain an implicit vector of each meal by vectorizing the food and performing feature extraction on the food vector;

a target template vector determining module, configured to determine, based on the attention mechanism model, a target template vector according to the implicit vector of each meal and the multiple template vectors, an enhanced vector obtaining module, configured to obtain an enhanced target template vector by performing an operation on the implicit vector of each meal with the target template vector to; and a target recommended recipe determining module, configured to output the target recommended recipe corresponding to a target template in response to classifying the enhanced target template vector through a neural network classifier.

In an optional embodiment, the implicit vector of each meal includes a second vector and a third vector, and the implicit vector obtaining module includes:

a first vector obtaining module, configured to determine the food of each meal in the historical dining data of the user, and obtain a first vector of each meal by vectorizing the food;

a second vector obtaining module, configured to obtain the second vector of each meal by performing an operation on the first vector of each meal using a first parameter matrix; and a third vector obtaining module, configured to obtain the third vector of each meal by performing an operation on the first vector of each meal using a second parameter matrix.

In an optional embodiment, the target template vector determining module includes:

a sample information obtaining module, configured to obtain multiple sets of sample information, where each set of sample information includes: the implicit vector of each meal and the multiple template vectors; and a model training module, configured to train the attention mechanism model by taking the implicit vector of each meal as an input, where probability values of the multiple template vectors as outputs, and determine a template vector with the largest probability value as the target template vector.

In an optional embodiment, the enhanced vector obtaining module includes:

an attention score calculating module, configured to calculate an attention score between the target template vector and the second vector of each meal; and a target template enhanced vector obtaining module, configured to obtain the enhanced target template vector by performing weighted average on the third vector of each meal according to the attention score corresponding to the implicit vector of each meal.

In an optional embodiment, the diet recommendation device further includes:

a meal preparation rule presetting module, configured to preset a meal preparation rule of each meal.

In an optional embodiment, the diet recommendation device further includes:

a mass determining module, configured to determine a mass of each food in the target recommended recipe according to a mass of each nutrient required for each meal.

In an optional embodiment, the mass determining module includes:

a nutrient mass determining module, configured to determine the mass of each nutrient required by the user for each meal according to basic information of the user; and a food mass determining module, configured to determine the mass of each food in the target recommended recipe according to the mass of each nutrient required for each meal.

In an optional embodiment, the nutrient mass determining module includes:

an energy determining module, configured to determine the energy required by the user for each meal according to the basic information of the user; and a mass of each nutrient determining module, configured to determine the mass of each nutrient required by the user for each meal according to the following relationships each between the energy required by the user for each meal and a nutrient required by the user for each meal:

$$\begin{cases} nutrientCount_1 = \text{energy} * \text{ratio}_1 / param_1 \\ nutrientCount_2 = \text{energy} * \text{ratio}_2 / param_2 \\ \quad \ldots \\ nutrientCount_n = \text{energy} * \text{ratio}_n / param_n \end{cases};$$

where $nutrientCount_n$ represents a mass of a $n^{th}$ nutrient; energy represents an energy value required by the user for each meal in a candidate recipe; $ratio_n$ represents a ratio coefficient of the $n^{th}$ nutrient to the energy value of each meal; and $param_n$ represents a converted energy coefficient of the $n^{th}$ nutrient; and n is a positive integer.

In an optional embodiment, the diet mass determining module is configured to determine the mass of each food in the target recommended recipe according to the following relationships each between a content of a nutrient in a candidate food contained in the target recommended recipe and a mass of the nutrient required for each meal:

$$\begin{cases} fat_1 * x_1 + fat_2 * x_2 + \ldots + fat_m * x_m = Count_1 \\ protein_1 * x_1 + protein_2 * x_2 + \ldots + protein_m * x_m = Count_2 \\ CHO_1 * x_1 + CHO_2 * x_2 + \ldots + CHO_m * x_m = Count_3 \end{cases};$$

where $fat_m$ represents a fat content of a $m^{th}$ food, $x_m$ represents a mass of the $m^{th}$ food, $Count_1$ represents a fat mass required by the user for each meal in the candidate recipe, $protein_m$ represents a protein content of the $m^{th}$ food, $Count_2$ represents a protein mass required by the user for each meal in the candidate recipe, $CHO_m$ represents a carbohydrate content of the $m^{th}$ food, $Count_3$ represents a carbohydrate mass required by the user for each meal in the candidate recipe; m is the number of food types in the target recommended recipe, and m is a positive integer.

In an optional embodiment, the mass determining module further includes:
a constraint condition presetting module, configured to preset, based on a preset meal preparation rule of each meal, a constraint condition of each nutrient required by the user according to the basic information of the user;
the food mass determining module is configured to determine the mass of each food in the target recommended recipe according to the constraint condition.

In an optional embodiment, the mass determining module further includes:
a nutrient content vectorizing module, configured to determine a content of each nutrient of each food in the target recommended recipe, and vectorize the content of each nutrient of each food; and
a food mass determining module, configured to output the mass of each food in the target recommended recipe by using the vector of the content of each nutrient as an input of a neural network model.

In an optional embodiment, a loss function of the neural network model in the food mass determining module is $Loss=\|\sigma-\sigma'\|^2+\text{regular term}$, where $\sigma=(Count_1, Count_2, Count_3)$, and the regular term is a preset constraint condition of each nutrient required by the user.

In an optional embodiment, the diet recommendation device further includes:
a candidate food determining module, configured to determine the multiple candidate foods according to a food knowledge graph and the basic information of the user.

In an optional embodiment, the candidate food determining module further includes:
a user basic information obtaining module, configured to obtain the basic information of the user, where the basic information includes at least one of age, gender, ethnicity, disease information, taste preference, and weight.

In an optional embodiment, the food mass determining module is further configured to:
output at least one of the mass of each nutrient required by the user for each meal and the mass of each food in the target recommended recipe.

The specific details of each module in the diet recommendation device have been described in detail in the corresponding diet recommendation method, so it will not be repeated here.

Each module in the above device can be a general purpose processor, including: a central processing unit, a network processor, etc.; it can also be a digital signal processor, an application specific integrated circuit, a field programmable gate array or other programmable logic devices, a discrete gate or a transistor logic device, a discrete hardware component. Each module can also be implemented in the form of software, firmware, etc. Each processor in the device may be an independent processor, or may be integrated together.

It should be noted that although modules or units of devices for executing functions are described above, such division of modules or units is not mandatory. In fact, features and functions of two or more of the modules or units described above may be embodied in one module or unit in accordance with the embodiments of the present disclosure. Alternatively, the features and functions of one module or unit described above may be further divided into multiple modules or units.

It should be understood that the present disclosure is not limited to the precise structures that have been described above and shown in the drawings, and various modifications and changes can be made without departing from the scope thereof. The scope of the present disclosure is limited only by the appended claims.

What is claimed is:

1. A computer-implemented diet recommendation method performed by a server computing device or a terminal computing device, the server computing device or the terminal computing device comprising a central processing unit (CPU), and an input portion connected to an input/output (I/O) interface, the method comprising:
receiving, by the input portion, historical dining data; and
reading, by the CPU, the historical dining data, and determining, based on multiple candidate foods and the historical dining data, a target recommended recipe by using a recommendation model;
determining energy required by a user for each meal according to basic information of the user;
determining a mass of each nutrient required by the user for each meal according to following relationships each between the energy required by the user for each meal and a nutrient required by the user for each meal;

$$\begin{cases} nutrientCount_1 = energy * ratio_1 / param_1 \\ nutrientCount_2 = energy * ratio_2 / param_2 \\ \ldots \\ nutrientCount_n = energy * ratio_n / param_n \end{cases};$$

wherein $nutrientCount_n$ represents a mass of a $n^{th}$ nutrient, energy represents an energy value required by the user for each meal in a candidate recipe, $ratio_n$ represents a ratio coefficient of the $n^{th}$ nutrient to the energy value of each meal, and $param_n$ represents a converted energy coefficient of the $n^{th}$ nutrient; and n is a positive integer; and determining a mass of each food in the target recommended recipe according to following relationships each between a content of a nutrient in a candidate food contained in the target recommended recipe and a mass of the nutrient required for each meal:

$$\begin{cases} fat_1 * x_1 + fat_2 * x_2 + \ldots + fat_m * x_m = Count_1 \\ protein_1 * x_1 + protein_2 * x_2 + \ldots + protein_m * x_m = Count_2 \\ CHO_1 * x_1 + CHO_2 * x_2 + \ldots + CHO_m * x_m = Count_3 \end{cases}$$

wherein $fat_m$ represents a fat content of a $m^{th}$ food, $x_m$ represents a mass of the $m^{th}$ food, $Count_1$ represents a fat mass required by the user for each meal in the candidate recipe, $protein_m$ represents a protein content of the $m^{th}$ food, $Count_2$ represents a protein mass required by the user for each meal in the candidate recipe, $CHO_m$ represents a carbohydrate content of the $m^{th}$ food, and $Count_3$ represents a carbohydrate mass required by the user for each meal in the candidate recipe; m is a quantity of food types in the target recommended recipe, and m is a positive integer;

presetting, based on a preset meal preparation rule of each meal, a constraint condition of each nutrient required by the user according to the basic information of the user;

determining the mass of each food in the target recommended recipe according to the constraint condition, wherein the constraint condition on intake of carbohydrates includes: $c_1*x_1+c_2*x_2+ \ldots +c_m*x_m \leq Count_4$, where $c_m$ represents a sugar content of the $m^{th}$ food, and $Count_4$ represents a sugar mass required by the user for each meal in the target recommended recipe;

determining a content of each nutrient of each food in the target recommended recipe, and performing One-Hot encoding for the content of each nutrient of each food to obtain a content vector of each nutrient; and outputting the mass of each food in the target recommended recipe by using the content vector of each nutrient as an input to a neural network model and updating the neural network model according to a loss function, wherein the neural network model is obtained by training with a sample content vector of each nutrient as input and the mass of each food in the target recommended recipe as output, and the loss function of the neural network model is expressed as: $Loss = \|\sigma - \sigma'\|^2 + regular\ term$, wherein $\sigma = (Count_1, Count_2, Count_3, Count_4)$ includes the mass of each nutrient required by the user for each meal, $\sigma'$ represents a mass of each nutrient required by the user for each meal predicted by the neural network model, and the regular term is a preset constraint condition of each nutrient required by the user.

2. The diet recommendation method of claim 1, wherein determining, based on the multiple candidate foods and the historical dining data, the target recommended recipe by using the recommendation model comprises:
constructing a hierarchical graph model based on the multiple candidate foods; and
determining, based on the historical dining data, the target recommended recipe by using the hierarchical graph model according to a random walk algorithm.

3. The diet recommendation method of claim 1, wherein the method further comprises: outputting at least one of the mass of each nutrient required by the user for each meal and the mass of each food in the target recommended recipe.

4. The diet recommendation method of claim 2, wherein determining, based on the historical dining data, the target recommended recipe by using the hierarchical graph model according to the random walk algorithm comprises:
initializing a weight of each edge in the hierarchical graph model;
updating the weight of each edge according to the historical dining data of a user; and
determining candidate foods contained in a path with a largest weight as the target recommended recipe.

5. The diet recommendation method of claim 4, wherein determining the candidate foods contained in the path with the largest weight as the target recommended recipe further comprises:
obtaining, based on the weight of the path corresponding to the target recommended recipe, a probability of the user selecting the target recommended recipe as a first probability value;
obtaining probabilities of multiple other users selecting the target recommended recipe as second probability values; and
determining a probability of the user selecting the target recommended recipe based on the first probability value and the second probability values.

6. The diet recommendation method of claim 1, wherein determining the target recommended recipe by using the recommendation model based on the multiple candidate foods and the historical dining data further comprises: determining the target recommended recipe by using an attention mechanism model based on the multiple candidate foods and the historical dining data.

7. The diet recommendation method of claim 6, wherein determining the target recommended recipe by using the attention mechanism model based on the multiple candidate foods and the historical dining data comprises:
presetting multiple templates for a meal preparation rule of each meal based on the multiple candidate foods;
obtaining multiple template vectors by vectorizing the multiple templates;
determining a food of each meal in the historical dining data of a user,
obtaining an implicit vector of each meal by vectorizing the food and performing feature extraction on the food vector;
obtaining an enhanced target template vector by performing an operation on the implicit vector of each meal with a target template vector; and
outputting the target recommended recipe corresponding to a target template in response to classifying the enhanced target template vector through a neural network classifier.

8. The diet recommendation method of claim 7, wherein the implicit vector of each meal comprises a second vector and a third vector; the determining the food of each meal in the historical dining data of the user, and the obtaining the implicit vector of each meal by vectorizing the food and performing the feature extraction on the food vector comprises:
- determining the food of each meal in the historical dining data of the user;
- obtaining a first vector of each meal by vectorizing the food;
- obtaining the second vector of each meal by performing an operation on the first vector of each meal using a first parameter matrix; and
- obtaining the third vector of each meal by performing an operation on the first vector of each meal using a second parameter matrix.

9. The diet recommendation method of claim 7, wherein the method further comprises:
- obtaining multiple sets of sample information, wherein each set of sample information comprises: the implicit vector of each meal and the multiple template vectors;
- training the attention mechanism model by taking the implicit vector of each meal as input, wherein probability values of the multiple template vectors are outputs; and
- determining a template vector with the largest probability value as the target template vector.

10. The diet recommendation method of claim 8, wherein obtaining the enhanced target template vector by performing the operation on the implicit vector of each meal with the target template vector comprises:
- calculating an attention score between the target template vector and the second vector of each meal; and
- obtaining the enhanced target template vector by performing weighted average on the third vector of each meal according to the attention score corresponding to the implicit vector of each meal.

11. A non-transitory computer-readable storage medium with a computer program stored thereon, wherein the computer program, when executed by at least one hardware processor, implements a method, comprising:
- obtaining historical dining data; and
- determining, based on multiple candidate foods and the historical dining data, a target recommended recipe by using a recommendation model;
- determining energy required by a user for each meal according to basic information of the user;
- determining a mass of each nutrient required by the user for each meal according to following relationships each between the energy required by the user for each meal and a nutrient required by the user for each meal;

$$\begin{cases} nutrientCount_1 = energy * ratio_1 / param_1 \\ nutrientCount_2 = energy * ratio_2 / param_2 \\ \ldots \\ nutrientCount_n = energy * ratio_n / param_n \end{cases};$$

wherein $nutrientCount_n$ represents a mass of a $n^{th}$ nutrient, energy represents an energy value required by the user for each meal in a candidate recipe, $ratio_n$ represents a ratio coefficient of the $n^{th}$ nutrient to the energy value of each meal, and $param_n$ represents a converted energy coefficient of the $n^{th}$ nutrient; and n is a positive integer; and
- determining a mass of each food in the target recommended recipe according to following relationships each between a content of a nutrient in a candidate food contained in the target recommended recipe and a mass of the nutrient required for each meal:

$$\begin{cases} fat_1 * x_1 + fat_2 * x_2 + \ldots + fat_m * x_m = Count_1 \\ protein_1 * x_1 + protein_2 * x_2 + \ldots + protein_m * x_m = Count_2 \\ CHO_1 * x_1 + CHO_2 * x_2 + \ldots + CHO_m * x_m = Count_3 \end{cases};$$

wherein $fat_m$ represents a fat content of a $m^{th}$ food, $x_m$ represents a mass of the $m^{th}$ food, $Count_1$ represents a fat mass required by the user for each meal in the candidate recipe, $protein_m$ represents a protein content of the $m^{th}$ food, $Count_2$ represents a protein mass required by the user for each meal in the candidate recipe, $CHO_m$ represents a carbohydrate content of the $m^{th}$ food, and $Count_3$ represents a carbohydrate mass required by the user for each meal in the candidate recipe; m is a quantity of food types in the target recommended recipe, and m is a positive integer;
presetting, based on a preset meal preparation rule of each meal, a constraint condition of each nutrient required by the user according to the basic information of the user;
determining the mass of each food in the target recommended recipe according to the constraint condition, wherein the constraint condition on intake of carbohydrates includes: $c_1*x_1+c_2*x_2+ \ldots +c_m*x_m \leq Count_4$, where $c_m$ represents a sugar content of the $m^{th}$ food, and $Count_4$ represents a sugar mass required by the user for each meal in the target recommended recipe;
determining a content of each nutrient of each food in the target recommended recipe, and performing One-Hot encoding for the content of each nutrient of each food to obtain a content vector of each nutrient; and
outputting the mass of each food in the target recommended recipe by using the content vector of each nutrient as an input to a neural network model and updating the neural network model according to a loss function, wherein the neural network model is obtained by training with a sample content vector of each nutrient as input and the mass of each food in the target recommended recipe as output, and the loss function of the neural network model is expressed as: Loss=$\|\sigma-\sigma'\|^2$+regular term,
wherein $\sigma=(Count_1, Count_2, Count_3, Count_4)$ includes the mass of each nutrient required by the user for each meal, $\sigma'$ represents a mass of each nutrient required by the user for each meal predicted by the neural network model, and the regular term is a preset constraint condition of each nutrient required by the user.

12. An electronic device, comprising:
at least one hardware processor; and
a memory storing program instructions executable by the at least one hardware processor that, when executed, direct the at least one hardware processor to execute a method, comprising:
- obtaining historical dining data; and
- determining, based on multiple candidate foods and the historical dining data, a target recommended recipe by using a recommendation model;
- determining energy required by a user for each meal according to basic information of the user;
- determining a mass of each nutrient required by the user for each meal according to following relationships each between the energy required by the user for each meal and a nutrient required by the user for each meal;

$$\begin{cases} nutrientCount_1 = energy * ratio_1 / param_1 \\ nutrientCount_2 = energy * ratio_2 / param_2 \\ \vdots \\ nutrientCount_n = energy * ratio_n / param_n \end{cases} ;$$

wherein $nutrientCount_n$ represents a mass of a $n^{th}$ nutrient, energy represents an energy value required by the user for each meal in a candidate recipe, $ratio_n$ represents a ratio coefficient of the $n^{th}$ nutrient to the energy value of each meal, and $param_n$ represents a converted energy coefficient of the $n^{th}$ nutrient; and n is a positive integer; and determining a mass of each food in the target recommended recipe according to following relationships each between a content of a nutrient in a candidate food contained in the target recommended recipe and a mass of the nutrient required for each meal:

$$\begin{cases} fat_1 * x_1 + fat_2 * x_2 + \ldots + fat_m * x_m = Count_1 \\ protein_1 * x_1 + protein_2 * x_2 + \ldots + protein_m * x_m = Count_2 \\ CHO_1 * x_1 + CHO_2 * x_2 + \ldots + CHO_m * x_m = Count_3 \end{cases} ;$$

wherein $fat_m$ represents a fat content of a $m^{th}$ food, $x_m$ represents a mass of the $m^{th}$ food, $Count_1$ represents a fat mass required by the user for each meal in the candidate recipe, $protein_m$ represents a protein content of the $m^{th}$ food, $Count_2$ represents a protein mass required by the user for each meal in the candidate recipe, $CHO_m$ represents a carbohydrate content of the $m^{th}$ food, and $Count_3$ represents a carbohydrate mass required by the user for each meal in the candidate recipe; m is a quantity of food types in the target recommended recipe, and m is a positive integer;

presetting, based on a preset meal preparation rule of each meal, a constraint condition of each nutrient required by the user according to the basic information of the user;

determining the mass of each food in the target recommended recipe according to the constraint condition, wherein the constraint condition on intake of carbohydrates includes: $c_1*x_1+c_2*x_2+ \ldots +c_m*x_m \leq Count_4$, where $c_m$ represents a sugar content of the $m^{th}$ food, and $Count_4$ represents a sugar mass required by the user for each meal in the target recommended recipe;

determining a content of each nutrient of each food in the target recommended recipe, and performing One-Hot encoding for the content of each nutrient of each food to obtain a content vector of each nutrient; and outputting the mass of each food in the target recommended recipe by using the content vector of each nutrient as an input to a neural network model and updating the neural network model according to a loss function, wherein the neural network model is obtained by training with a sample content vector of each nutrient as input and the mass of each food in the target recommended recipe as output, and the loss function of the neural network model is expressed as: Loss=$\|\sigma-\sigma'\|^2$+regular term, wherein $\sigma=(Count_1, Count_2, Count_3, Count_4)$ includes the mass of each nutrient required by the user for each meal, $\sigma'$ represents a mass of each nutrient required by the user for each meal predicted by the neural network model, and the regular term is a preset constraint condition of each nutrient required by the user.

13. The device of claim 12, wherein the at least one hardware processor is further directed to:

construct a hierarchical graph model based on the multiple candidate foods; and determine, based on the historical dining data, the target recommended recipe by using the hierarchical graph model.

14. The device of claim 12, wherein the at least one hardware processor is further directed to: determine the target recommended recipe by using an attention mechanism model based on the multiple candidate foods and the historical dining data.

* * * * *